United States Patent
Gangopadhyay et al.

(10) Patent No.: US 11,796,473 B2
(45) Date of Patent: Oct. 24, 2023

(54) DETECTION OF BIOMARKERS USING PLASMONIC GRATINGS

(71) Applicant: The Curators of the University of Missouri, Columbia, MO (US)

(72) Inventors: Shubhra Gangopadhyay, Columbia, MO (US); Sangho Bok, Washington, UT (US); Cherian Joseph Mathai, Columbia, MO (US); Keshab Gangopadhyay, Columbia, MO (US); Sheila Grant, Columbia, MO (US); Aaron Wood, Tucson, AZ (US); Syed Barizuddin, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 445 days.

(21) Appl. No.: 16/614,573

(22) PCT Filed: Jul. 11, 2018

(86) PCT No.: PCT/US2018/041621
§ 371 (c)(1),
(2) Date: Nov. 18, 2019

(87) PCT Pub. No.: WO2019/014335
PCT Pub. Date: Jan. 17, 2019

(65) Prior Publication Data
US 2020/0173922 A1  Jun. 4, 2020

Related U.S. Application Data

(60) Provisional application No. 62/531,565, filed on Jul. 12, 2017.

(51) Int. Cl.
*B82Y 40/00* (2011.01)
*G01N 21/64* (2006.01)
(Continued)

(52) U.S. Cl.
CPC ....... *G01N 21/648* (2013.01); *C07K 16/1289* (2013.01); *G01N 21/6428* (2013.01);
(Continued)

(58) Field of Classification Search
None
See application file for complete search history.

(56) References Cited

U.S. PATENT DOCUMENTS 9,315,566 B2    4/2016  Macary et al.
2006/0034729 A1  2/2006  Poponin
(Continued)

FOREIGN PATENT DOCUMENTS

CN      106442468 A    2/2017
WO    WO2015/011980  *  1/2015

OTHER PUBLICATIONS

Sonato et al., "A surface acoustic wave (SAW)-enhanced grating-coupling phase-interrogation surface plasmon resonance (SPR) microfluidic biosensor", The Royal Society of Chemistry, 16, pp. 1224-1233, 2016. (Year: 2016).*
(Continued)

*Primary Examiner* — Rebecca M Giere
(74) *Attorney, Agent, or Firm* — Erise IP, P.A.

(57) ABSTRACT

The invention broadly relates techniques for imaging and medical diagnosis and, more particularly, to the fabrication of flexible plasmonic gratings and the use thereof in detection of biomarkers. A first aspect of the invention provides for techniques for the fabrication of novel, flexible plasmonic gratings that can be inexpensively fabricated onto fiber optic cables, flexible films and substrates with non-uniform surfaces to enhance the imaging resolution. A second aspect of the invention provides for an ultra-high sensitivity (single molecule counting) biomarker detection platform useable for medical diagnosis based on a fluores- (Continued)

cent sandwich ELISA assay performed on a plasmonic grating platform incorporated with a fluorescence detection unit.

20 Claims, 5 Drawing Sheets

(51) Int. Cl.
    *C07K 16/12*     (2006.01)
    *G01N 21/552*     (2014.01)

(52) U.S. Cl.
    CPC ............ *B82Y 40/00* (2013.01); *G01N 21/554* (2013.01); *G01N 2021/6439* (2013.01)

(56) References Cited

U.S. PATENT DOCUMENTS

2008/0278722 A1* 11/2008 Cunningham ..... G01N 21/6428
    356/317
2014/0226207 A1     8/2014 Gangopadhyay et al.

OTHER PUBLICATIONS

Mohapatra et al., "Facile fabrication of polymer nanograting for developing cost-effective plasmonic regractive index sensor using UV nanoimprint lithography", The International Conference on Fiber Optics and Photonics, pp. 1-3, 2016. (Year: 2016).*

Pale et al., Fluorescene-enhancing plasmonic silver nanostructures using azopolymer lithography, RSC Advances, 2016, 6, pp. 48129-48136. (Year: 2016).*

Tuteja et al., Graphene-gated biochip for the detection of cardiac marker Troponin I, Analytica Chimica Acta 809 (2014) pp. 148-154. (Year: 2014).*

Kim et al., Simple fabrication of hydrophilic nanochannels using the chemical bonding between activated ultrathin PDMS layer and cover glass by oxygen plasma, Lab Chip, 2011, 11, pp. 348-353. (Year: 2011).*

Roy et al., Surface analysis, hydrophilic enhancement, ageing behavior and flow in plasma modified cyclic olefin copolymer (COC)-based microfluidic devices, Sensors and Actuators B, 150, 2010, pp. 537-549. (Year: 2010).*

Kim et al., "Simple Route to Hydrophilic Microfluidic Chip Fabrication Using an Ultraviolet (UV)-cured polymer", Advanced Functional Materials, 2007, 17, pp. 3493-3498. (Year: 2007).*

Wood et al., "Influence of silver grain size, roughness, and profile on the extraordinary fluorescence enhancement capabilities of grating coupled surface plasmon resonance", RSC Adv., 2015, 5, pp. 78534-78544. (Year: 2015).*

PCT Patent Application No. PCT/US2018/041621 International Search Report and Written Opinion dated Nov. 1, 2018.

* cited by examiner

DETECTION OF BIOMARKERS USING PLASMONIC GRATINGS

RELATED APPLICATIONS

This patent application claims priority benefit, with regard to all common subject matter, of earlier-filed PCT Intl App. No. PCTUS2018/041621, filed Jul. 11, 2018, and entitled "DETECTION OF BIOMARKERS USING PLASMONIC GRATINGS," which claims priority to U.S. Provisional Patent Application No. 62/531,565, filed Jul. 12, 2017 and entitled DETECTION OF BIOMARKERS USING PLASMONIC GRATINGS. This non-provisional patent application also shares certain subject matter with earlier-filed U.S. patent application Ser. No. 14/081,353 filed Nov. 15, 2013 and entitled NANO-GAP GRATING DEVICES WITH ENHANCED OPTICAL PROPERTIES AND METHODS OF FABRICATION and with U.S. patent application Ser. No. 15/543,150 filed Jul. 12, 2017 and entitled FABRICATION OF MULTILAYER NANOGRATING STRUCTURES, which claims priority to U.S. Provisional Patent Application No. 62/296,253, filed Feb. 17, 2016, and entitled "FABRICATION OF MULTILAYER NANOGRATING STRUCTURES.". The identified earlier-filed patent applications are hereby incorporated by reference in their entirety into the present application.

GOVERNMENT LICENSE RIGHTS

This invention was made with Government support under NSF grant number 1562831 awarded by the National Science Foundation. The Government has certain rights in this invention.

BACKGROUND

1. Field

The invention broadly relates techniques for imaging and medical diagnosis and, more particularly, to the fabrication of flexible plasmonic gratings and the use thereof in detection of biomarkers.

2. Related Art

Existing techniques for medical diagnosis are slow, cumbersome, and expensive. One example is the diagnosis of tuberculosis. The global tuberculosis report from World Health Organization (WHO) with data compiled from 205 countries notes that despite all the advances in technology and receding fatality rates, 1.5 million people died, and 9.6 million people were ill in the year 2014. The report also states, "Detection and treatment gaps must be addressed, and new tools developed" for better diagnosis of tuberculosis.

Even though there are many methods available for TB detection, such as culture tests, nucleic acid tests, skin tests, sputum smear, chest X-ray, and drug susceptibility tests, each one has its own limitations as a diagnostic method. For example, a typical tuberculosis culture test requires 21 days to generate results while more sophisticated molecular diagnostic tests can cost upwards of non-17,000 for the instrumentation and $17 for each test cartridge, even after subsidies Advanced molecular tests like Xpert MTD/RIF only detect resistance to Rifampin and Isoniazid. As a result, a positive result in such a test must be confirmed by a culture test. Additionally, such techniques utilize Polymerase Chain Reaction (PCR) as a detection technique, which amplifies unwanted DNA as well and therefore limits its detection sensitivity. Furthermore, the Xpert system is expensive, costing $17,000 for the instrumentation and $17 for each test cartridge, even after subsidies. Other tests including T-spot and IGRA can cost more than $75 for each test. As such, a rapid, low cost test that can detect tuberculosis early and with specificity is clearly needed. The situation is similar (or even worse) for a number of other diseases, including Zika, Ebola, HIV, cancer, etc.

Embodiments of the invention address the above-described need by providing for low-cost, fast, and highly specific diagnostic tools and techniques. In particular, embodiments of the invention provide for a platform for single molecule and ultra-sensitive detection of biomarkers. This system has a wide dynamic range, including ultra-low concentrations (in the femtogram per milliliter range). Some embodiments of the system are based on a fluorescent sandwich ELISA assay (or other assay technique such as a competitive binding fluoroimmunoassay) performed on the plasmonic grating platform incorporated with a fluorescence detection unit that is simple and easy to use. The plasmonic grating is capable of enhancing the fluorescent intensity by a factor of at least 100 as compared to a glass substrate. This enhancement is the result of excellent light coupling properties and superior signal-to-noise ratio of the novel plasmonic grating. With such enhancement, the system can detect ultra-low concentrations of the biomarkers, down to a single molecule of the biomarker (such as lipids, proteins, DNA, RNA, etc.), by using a simple epi-fluorescence microscope. Directional excitation and emission coupling further enhance the signal-to-noise ratio and improve performance.

A proof-of-concept implementation of the system can provide diagnosis of tuberculosis based on the Lipoarabinomannan (LAM) and Interferon gamma (IFN-g) biomarkers non-invasively (e.g., in saliva or urine), for a system cost of approximately $1000 with a per-test cost of $5 or less, while potentially providing result in 3 hrs. The specificity, time, cost, and ease of use makes this system one-of-a-kind and a substantive innovation in the diagnostic market. With such vast implications worldwide, embodiments of the invention are well suited to play a crucial role in addressing the need for an early, non-invasive, and inexpensive diagnostic system.

Advantages of the invention include ultra-sensitive biomarker detection (down to the single-molecule level); adaptability to any disease or condition with the use of corresponding immunoassay immobilization; non-invasive detection (e.g., detecting biomarkers in saliva or urine); greatly reduced equipment costs (epi-fluorescence microscope paired with a smartphone compared with a million-dollar confocal microscope or similar system); greatly decreased detection time; and early detection capability.

SUMMARY

In a first embodiment, the invention includes an apparatus for ultra-sensitive biomarker detection, comprising a fluorescence-enhancing nanoscale plasmonic grating platform including a sample area an excitation light source configured to illuminate the sample area of the fluorescence-enhancing nanoscale plasmonic grating platform, an epi-fluorescence magnifying assembly positioned to view the sample area of the fluorescence-enhancing nanoscale plasmonic grating platform, a camera positioned to image the sample area of the fluorescence-enhancing nanoscale plasmonic grating platform through the epi-fluorescence microscope, and a display configured to display imagery from the camera.

In a second embodiment, the invention includes a method of fabricating a fluorescence-enhancing, flexible, nanoscale plasmonic grating, comprising the steps of exposing a master mold to a hydrophilicity agent, spin coating the master mold with a grating material, curing the grating material to produce a nanoscale polymer grating in the master mold, removing the nanoscale polymer grating from the master mold, coating the nanoscale polymer grating in a fluorescence-enhancing reflective layer, coating the fluorescence-enhancing reflective layer with a protective capping layer.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

Figure 1:
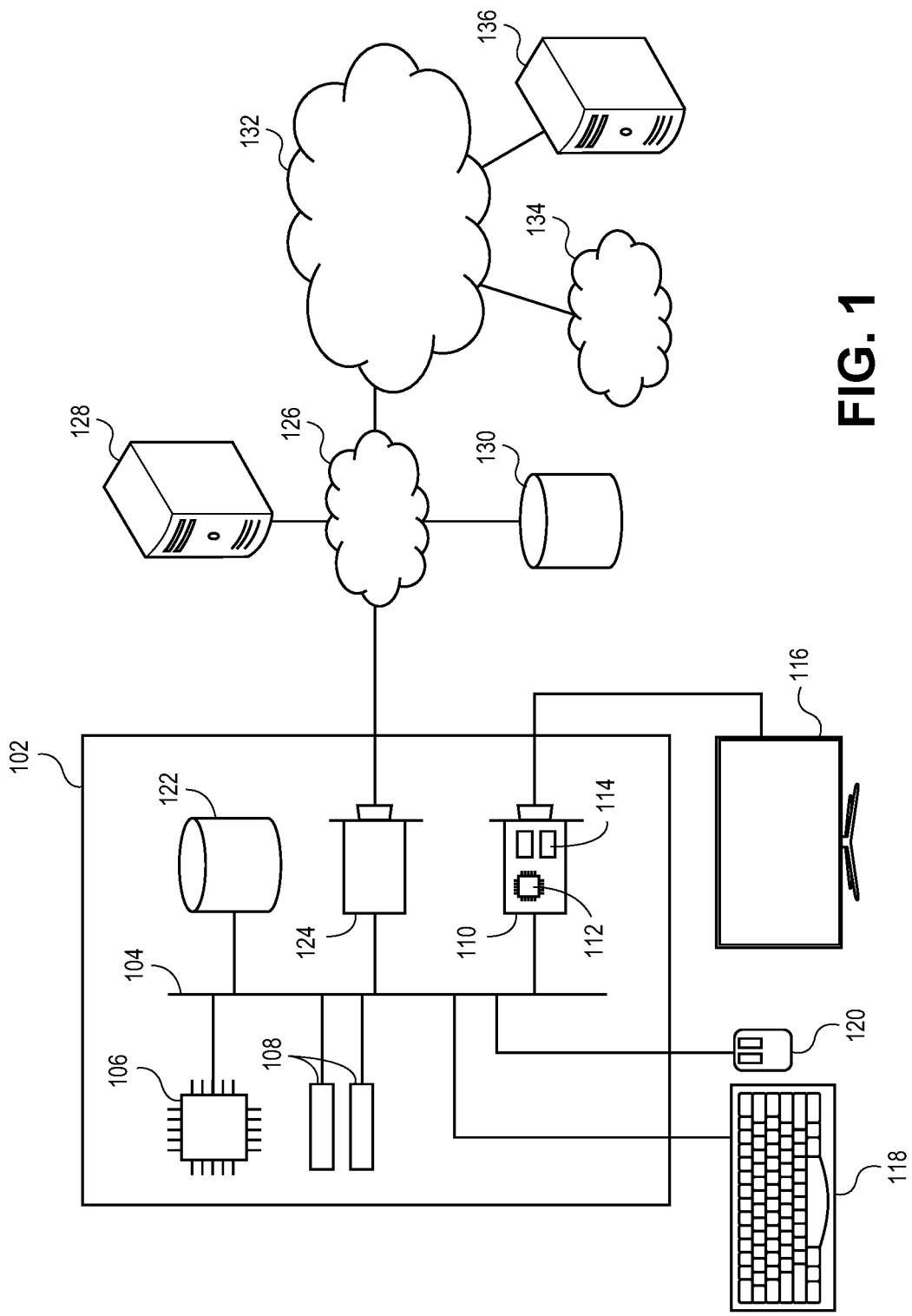
FIG. 1 depicts an exemplary hardware platform for certain embodiments of the invention.

The drawing figures do not limit the invention to the specific embodiments disclosed and described herein. The drawings are not necessarily to scale, emphasis instead being placed upon clearly illustrating the principles of the invention.

DETAILED DESCRIPTION

At a high level, the invention includes an ultra-sensitive diagnostic system based on low-cost soft lithography nanostructured plasmonic grating technology that non-invasively (in urine or saliva) detects specific biomarkers, such as Lipoarabinomannan (LAM) and Interferon gamma (IFN-g) for tuberculosis (TB) diagnosis. This system has a wide dynamic range including ultra-low concentrations (femtogram per milliliter or less). The proposed system is based on a fluorescent sandwich ELISA assay performed on the plasmonic grating platform incorporated with a fluorescence detection unit that is simple and easy to use. The novel plasmonic gratings are capable of enhancing the fluorescent intensity by a factor of at least 100 times as compared to a glass substrate. The enhancement is the result of excellent light coupling properties and superior signal-to-noise ratio of the plasmonic grating. Directional excitation and emission coupling will further enhance the signal-to-noise ratio. The specificity, time, cost, and ease of use makes this system unique and a substantive innovation in the diagnostic market. The disclosed plasmonic gratings are a "platform" technology that can be easily adapted to the diagnosis of other diseases including Zika, Ebola, HIV, cancer, etc., using appropriate assay techniques and methods of fluorescent detection.

Certain embodiments of the invention may include novel flexible plasmonic gratings, fabrication techniques for which are discussed herein. The flexible plasmonic gratings of the invention can be used in the above-described fluorescent detection and imaging applications, and also in other applications of nanoscale gratings benefiting from a flexible grating. In particular, such embodiments result in flexible, simple, low cost, polyurethane plasmonic gratings that can be coated in silver films to enhance the fluorescent emission intensity of nearby fluorescent dye molecules. These fabrication techniques provide the ability to inexpensively fabricate plasmonic gratings onto the tips of fiber optic cables, flexible films and substrates with non-uniform surfaces to enhance the imaging resolution.

A first aspect of the invention provides for techniques for the fabrication of novel, flexible plasmonic gratings that can be inexpensively fabricated onto fiber optic cables, flexible films and substrates with non-uniform surfaces to enhance the imaging resolution. A second aspect of the invention provides for an ultra-high sensitivity biomarker detection platform useable for medical diagnosis based on a fluorescent sandwich ELISA assay (as well as other assay techniques) performed on a plasmonic grating platform incorporated with a fluorescence detection unit.

A first benefit of the invention is ultra-sensitive detection of specific biomarkers, including tuberculosis-specific biomarkers. The main limitation of conventional immunoassays is not being able to detect extremely small fluorescent signals from the ultra-low concentration of biomarkers. The novel plasmonic gratings of the invention alleviate this problem due to their extremely efficient light coupling, reduced scattering, high signal-to-noise ratio and directional excitation/emission. This enables a fluorescence enhancement factor of over 100 as compared to conventional glass substrates or polyurethane well plates. Such high enhancement translates to biomarker detection in the femtogram per milliliter range which in-turn enables earlier diagnosis.

A second benefit of the invention is faster detection of biomarkers. Commercial immunoassays require hours to days to achieve picogram per milliliter sensitivity. It is widely known that reducing reaction time reduces sensitivity in conventional detection methods. In comparison, embodiments of the invention can detect picogram-per-milliliter range concentrations in less than three hours after sample immobilization.

A third benefit of the invention is its low cost. A system in accordance with an embodiment of the invention utilizes a simplified design to exclude expensive optics like laser light sources, high-magnification objective lenses and filter cubes. Further, the use of 3-D printed parts to fabricate the system and use a smartphone as the detector will further reduce the cost.

Flexible Plasmonic Gratings

One aspect of the invention includes flexible plasmonic grating apparatus configurations and techniques for the fabrication thereof for use in fluorescent detection and imaging applications. Prior techniques, as disclosed in co-pending U.S. patent application Ser. No. 14/081,353 and in U.S. Provisional Patent Application No. 62/296,253 (the disclosures of which are hereby incorporated by reference in their entirety into this specification) resulted rigid gratings and required high-temperature heat treatments. This lack of flexibility and the necessity of heat treatments for our previously developed polymethylsilsesquioxane (PMSSQ)

gratings restricted the use of such gratings from being applied to flexible media such as fiber optic cables, polymer films, tapes, etc. Such media are used in many types of diagnostic devices such as catheter-based biosensors and wearable biosensors.

Embodiments of the present invention build on the previously developed gratings by using them as a mold for a more flexible polymer. For example, in one embodiment, gratings are made from polyurethane, resulting in a flexible, simple, low cost, polyurethane (PU) plasmonic grating that can be coated in silver films to enhance the fluorescent emission intensity of fluorescent dye molecules nearby to (for example, within 1 micrometer of) the surface of the silver film. These PU gratings are made using simple casting process that utilizes the PMSSQ gratings disclosed previously as a master mold. Three formulations of PU have been successfully used to fabricate PU gratings and are commercially available as UV-curable optical adhesives made by Norland Products Inc. sold under these names: Norland Optical Adhesive (NOA) 71, NOA 73, and NOA 81.

As a high-level outline of the process, initially a master mold on a rigid substrate is prepared. If this master mold is hydrophobic, it can be treated with a hydrophilicity agent, such as plasma (e.g., oxygen or carbon dioxide plasma) or ozone to convert surface methyl groups to hydroxyl groups and carboxyl groups. Next, the master mold can be spin-coated with a grating material (e.g., a UV-curable optical adhesive) to produce a flexible film. This film can then be applied to a second substrate and treated so as to adhere thereto. The grating material assembly can then be cured appropriately and the grating assembly removed from the master mold. In some embodiments, silicon wafers (etched appropriately) can be used as the master mold. In other embodiments, a silica wafer with dispersed aluminum particles is used as the master mold.

A fabrication of polyurethane gratings on plastic cover slips is given as a concrete example of this process. To fabricate a polyurethane grating on a flexible coverslip, a PMSSQ grating on a glass or silicon substrate is exposed to oxygen plasma for 30 seconds at a power of 7 Watts to increase hydrophilicity. The PMSSQ grating is immediately spin-coated with NOA 71 at a speed between 200 and 500 RPM for 30 seconds to produce a polyurethane film with a thickness between 110 and 40 micrometers. A plastic coverslip is placed over the spin-coated film and vacuum desiccated for 10 min to remove entrapped air under the coverslip. The PMSSQ, PU film, and coverslip assembly is placed under a 6 Watt UV lamp for 40 min. After UV exposure, the PU film is removed by cutting along the perimeter of the coverslip and peeling the coverslip from the PMSSQ grating. In another embodiment, thicker films of PU between 500 micrometers and 2 millimeters can be fabricated to form stand-alone flexible gratings (i.e., without a substrate such as the cover slip) that have applications in wearable biosensor systems.

One application of these flexible nanogratings is to image nanoparticles with improved resolution when placed within approximately 200 nanometers of the nanoparticles. Plasmonic gratings can project near-field image information out to the far field where it can be detected by a CMOS or CCD camera. The projection of image information by a plasmonic grating is referred to in other scientific literature as a "far field superlens" effect. In the single molecule imaging concentration range, two populations of single molecule imaging behavior were observed behavior. First, a diffraction-limited airy disc pattern was observed which is typically observed when using flat silver or quartz slides as a substrate. The second, and largest population, however, exhibited a split emission pattern that was linked to an individual single molecule based on its single step photobleaching characteristics. The second population is best described as single molecule surface plasmon coupled emission (SPCE). Prior techniques for SPCE are limited to the bulk measurement many inches from the sample. Embodiment of the invention thus provide a novel technique for studying the SPCE from individual molecules and greatly enhance single molecule spectroscopy measurements. SPCE of individual molecules further increases imaging resolution via the ability of the plasmonic grating to project near-field sub-diffraction limit image information into the far-field, the "far field superlens" effect described above.

Adding flexibility to the plasmonic gratings enables the grating to conform to the sample surface and place the gratings closer to the objects of interest on the sample. In other aspects, various nanograting configurations provide improved resolution to image nanoparticles that are placed within approximately 200 nm of the nanograting configuration to project near-field image information out to the far field where it can be detected by CMOS and CCD cameras, or analogs thereof.

Ultra-Sensitive Detection of Biomarkers Using Plasmonic Gratings

Another aspect of the invention involves the use of nanoscale plasmonic gratings for the detection of biomarkers. In particular, a fluorescent sandwich enzyme-linked immunosorbent assay (ELISA) assay is performed on a plasmonic grating platform incorporated with a fluorescence detection unit. The use of the novel fluorescence-enhancing gratings disclosed above and in co-pending U.S. patent application Ser. No. 14/081,353 and in U.S. Provisional Patent Application No. 62/296,253 (the disclosures of which are hereby incorporated by reference in their entirety into this specification) allows for detection of biomarkers in ultra-low concentrations (femtogram per milliliter or less).

In one embodiment, the platform comprises a grating sensing unit integrated with an imaging/detection system. The grating sensing unit may incorporate a flexible plasmonic grating (as disclosed above) or may incorporate a rigid plasmonic grating instead. Broadly speaking, any type of plasmonic grating disclosed above or in the above-incorporated applications is contemplated as being useable with various embodiments of the invention. Other components of the platform include a Light Emitting Diode (LED) of a suitable wavelength as an angle adjustable excitation light source, batteries, and housing to block ambient light to prevent interference of fluorescence measurement. In some embodiment, the LED can be a laser diode. In some such embodiment, the diode output may be circularized by means of a microlens, by an offset anamorphic prism assembly, or by being coupled into a fiber optic cable. In some aspects, the camera of a smartphone can be used as a detector and the processor of the smartphone can be used for analyzing the data using an application running on the phone to avoid the need to transmit imaging data for remote analysis.

In order to validate this platform, proof-of-concept detection of various biological analytes was performed. In particular, Lipoarabinomannan (LAM), Interferon Gamma (IFN-g), Prostate Specific Antigen (PSA), Sodium and Cortisol have already been tested as biomarkers for proof-of-concept in the initial studies, and are contemplated as biomarkers to be detected by the invention. Embodiments of the invention allow for an early detection platform to detect extremely low levels of these and other biomarkers. In particular, the superior optical properties of the novel plasmonic gratings allow the platform to enhance the smallest of fluorescence signals (due to extremely efficient light coupling and the enhanced signal-to-noise ratio) emanating from a fluorescently labeled sandwich assay (such as an ELISA assay). Prior technologies are limited in their ability to resolve the S/N ratio for ultra-sensitive concentrations, even with sophisticated detectors. By contrast, in the disclosed system, the fluorescence from the grating surface was detected using an epi-fluorescence microscope and a CMOS camera (such as a conventional CMOS camera found in a smartphone). The detected fluorescence correlates to the biomarker concentration, allowing concentration estimation. In detection tests for different biomarkers (LAM, IFN-g, PSA, etc.), detection levels as low as the femtograms-per-milliliter range have been observed, although the platform has a wide dynamic range of detection (from femtograms per milliliter or to micrograms per milliliter). Conventional techniques for immunoassays are limited to detection thresholds in the micrograms-per-milliliter range because of the high background making them impractical in the detection of picogram-per-milliliter concentrations or sub-picogram-per-milliliter concentrations. As such, the disclosed platform outperforms more laborious, invasive and complicated diagnostic tests in its specificity, simplicity of fabrication, detection thresholds, and ease of use, fast detection time and low production cost.

As one example of a diagnostic scenario, consider a diagnostic test for tuberculosis. To perform the diagnostic test, the specimen under test is placed on a grating platform immobilized with an anti-LAM antibody (or, depending on the particular biomarker being tested, an anti-IFN-g antibody) followed by the introduction of LAM. Antibodies for various biomarkers are typically available for sale commercially. After a predetermined amount of time, the surface is washed with a buffer such as PBS. A second solution containing a detection antibody (such as a biotinylated anti-LAM antibody) is introduced to the plasmonic grating surface followed by the introduction of the reporter antibody (after incubation of the previous step) tagged with a fluorophore (for example, a dye-labeled Streptavidin, such as Alexa Fluor® 568 Streptavidin). After this incubating step, the surface of the grating is washed to remove the excess antibody. The immunoassay immobilized grating is now ready to be imaged and is placed under the imaging system. The surface response in the form of the fluorescence is an Indicator of the biomarker bound to the anti-LAM antibody being reported by the fluorescent reporter antibody that is imaged. The amount of fluorescence corresponds to the concentration of the specific biomarker.

As a second example of a diagnostic scenario, consider an IFN-g assay performed in the urine to detect the tuberculosis biomarker noninvasively. The detection of IFN-g is important, as it is an indicator for many diseases. Using a fluorescent ELISA enables quick translation of this technology to the clinical laboratories. An anti-IFN-g (capture) antibody is immobilized on the surface of the plasmonic grating followed by exposure to a sample of human urine potentially containing IFN-g at a low concentration. Subsequently, the grating is treated with the anti-IFN-g antibody (detection antibody). The substrate is then washed to remove non-specific binding. Next, the grating surface is exposed to a signal antibody labeled with a fluorophore and the assay was imaged.

In practice, evaluations of the above-described LAM assay have demonstrated an ultra-sensitive lower limit of detection (LOD) of 1 femtogram per milliliter with fluorescence-based ELISA. The fluorescent intensities for higher concentrations are determined from the bulk due to the high density of fluorophores whereas, for lower concentrations, intensities are from the single fluorescent molecules.

In some embodiments, the invention may further include a microfluidic flow cell so as to require a lower sample volume, reduce contamination risk, and render the plasmonic gratings easier to handle and to image. In such embodiments, a plasmonic grating in accordance with the invention and as described above may be layered onto a microscope slide. A PLA flow cell is then placed on top of the microscope slide such that the sample or samples flow across the plasmonic grating. The PLA flow cell can then be covered and sealed by a glass coverslip to ensure sample integrity. Samples (and other test components) being tested can then be introduced to the plasmonic grating via the flow cell using a syringe. Any fluorescence from the test sample can then be imaged through the microscope slide. A person of ordinary skill in the art will appreciate that, in a similar fashion, plasmonic gratings in accordance with the invention can similarly be incorporated into a standard 96-wellplate kit as is used in ELISA testing.

Operational Environment for Embodiments of the Invention

Turning first to FIG. 1, an exemplary hardware platform for certain embodiments of the invention is depicted. Computer 102 can be a desktop computer, a laptop computer, a server computer, a mobile device such as a smartphone or tablet, or any other form factor of general- or special-purpose computing device. Depicted with computer 102 are several components, for illustrative purposes. In some embodiments, certain components may be arranged differently or absent. Additional components may also be present. Included in computer 102 is system bus 104, whereby other components of computer 102 can communicate with each other. In certain embodiments, there may be multiple busses or components may communicate with each other directly. Connected to system bus 104 is central processing unit (CPU) 106. Also attached to system bus 104 are one or more random-access memory (RAM) modules 108. Also attached to system bus 104 is graphics card 110. In some embodiments, graphics card 110 may not be a physically separate card, but rather may be integrated into the motherboard or the CPU 106. In some embodiments, graphics card 110 has a separate graphics-processing unit (GPU) 112, which can be used for graphics processing or for general purpose computing (GPGPU). Also on graphics card 110 is GPU memory 114. Connected (directly or indirectly) to graphics card 110 is display 116 for user interaction. In some embodiments no display is present, while in others it is integrated into computer 102. Similarly, peripherals such as keyboard 118 and mouse 120 are connected to system bus 104. Like display 116, these peripherals may be integrated into computer 102 or absent. Also connected to system bus 104 is local storage 122, which may be any form of computer-readable media, and may be internally installed in computer 102 or externally and removeably attached.

Computer-readable media include both volatile and nonvolatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-useable instructions, data structures, program modules, and other data representations.

Finally, network interface card (NIC) 124 is also attached to system bus 104 and allows computer 102 to communicate over a network such as network 126. NIC 124 can be any form of network interface known in the art, such as Ethernet, ATM, fiber, Bluetooth, Wi-Fi (i.e., the IEEE 802.11 family of standards), or cellular data (e.g., the GSM, EDGE, EV-DO, UTMS, WiMAX, HSPA+, LTE, LTE-A, or 5G standards). NIC 124 connects computer 102 to local network 126, which may also include one or more other computers, such as computer 128, and network storage, such as data store 130. Generally, a data store such as data store 130 may be any repository from which information can be stored and retrieved as needed. Examples of data stores include relational or object oriented databases, spreadsheets, file systems, flat files, directory services such as LDAP and Active Directory, or email storage systems. A data store may be accessible via a complex API (such as, for example, Structured Query Language), a simple API providing only read, write and seek operations, or any level of complexity in between. Some data stores may additionally provide management functions for data sets stored therein such as backup or versioning. Data stores can be local to a single computer such as computer 128, accessible on a local network such as local network 126, or remotely accessible over Internet 132. Local network 126 is in turn connected to Internet 132, which connects many networks such as local network 126, remote network 134 or directly attached computers such as computer 136. In some embodiments, computer 102 can itself be directly connected to Internet 132.

Figure 2:
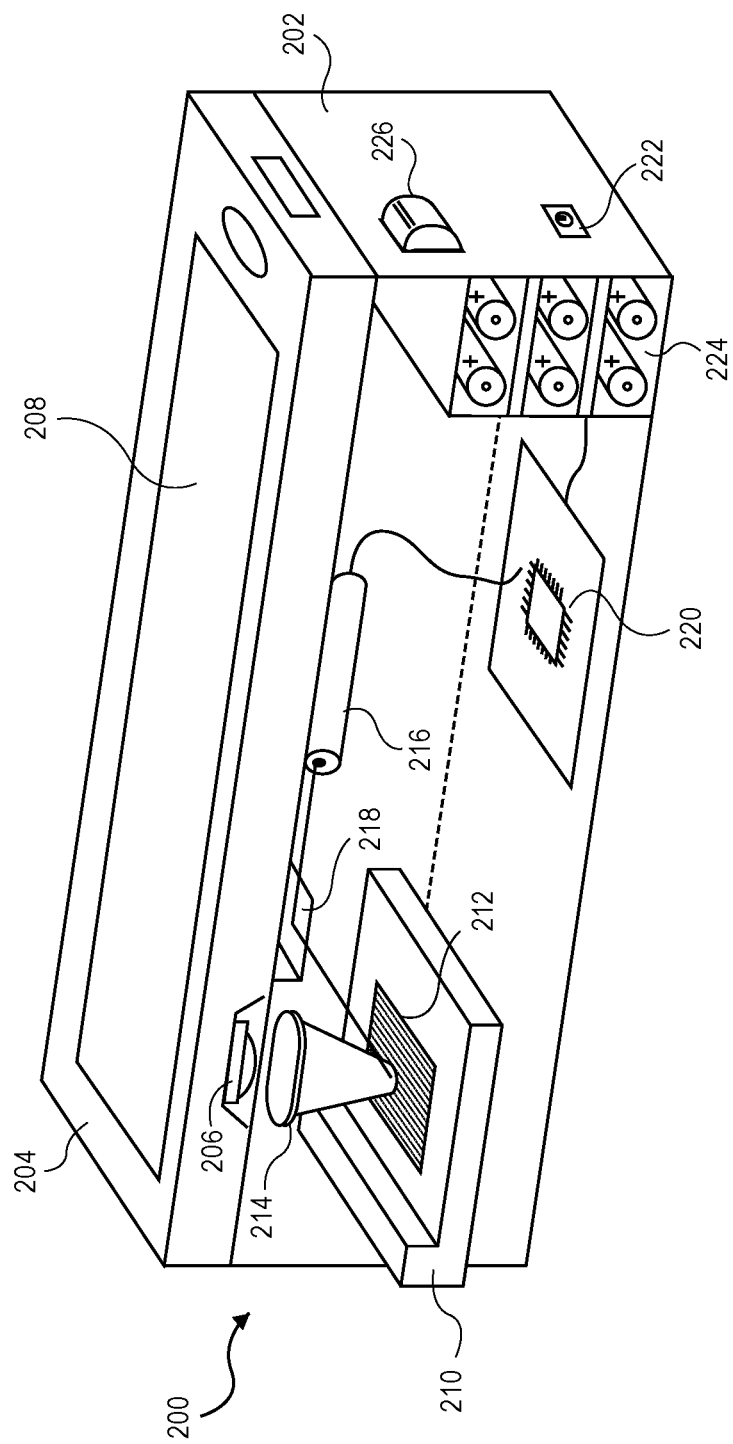
FIG. 2 depicts a test platform in accordance with embodiments of the invention.

Turning now to FIG. 2, a test platform in accordance with embodiments of the invention is depicted and referred to generally by reference numeral 200. Test platform 200 has the advantage of being a low-cost, portable system suitable for performing diagnostic tests in the field. As depicted, test platform 200 comprises housing 202, which contains the other components, provides the light source for the imaging and aligns the sample, light source, and sensing components. Housing 202 also blocks ambient light during the imaging process to improve diagnostic sensitivity.

In particular, test platform 200 utilizes smartphone 204 to provide the imaging, user interface, and data capture, storage and transmission functions of the imaging platform. In other embodiments of the invention, smartphone 004 may instead be a tablet, digital camera, or any other imaging device. Smartphone 204 includes a lens and charged-coupled device (CCD) sensor 206 for capturing the light being emitted and/or reflected from the sample while it is exposed to the light source provided by platform 200. Smartphone 204 also includes a touchscreen display 208 for displaying the captured imagery as well as for allowing the user to control the operation of test platform 208.

Platform 200 also includes a specimen receptacle 210 for receiving, supporting, and positioning grating 212 during the imaging process. In some embodiment of the invention, receptacle 210 slides out of housing 202 to receive a sample, and then slides back in to position it in alignment with sensor 206 for the imaging process. Grating 212, as described in additional detail elsewhere, is a nano-scale grating operable to enhance the fluorescence of the fluorophore-labeled biomarkers via surface plasmon resonance or any other suitable fluorescence enhancement technique. In particular, use of a plasmonic grating as grating 212 substantially improves image resolution such that single molecules can be imaged and enables the imaging of surface plasmon coupled emission (SPCE).

The light emitted and/or reflected from grating 212 is then captured, refocused, and filtered by external lens and emission filter 214. This may increase imaging sensitivity if, for example, light source 216 is a monochromatic light source. In some embodiments, excitement light source 216 is a laser diode. Light emitted from excitement light source 216 strikes mirror 218, where it is reflected onto grating 212 as positioned by receptacle 210 and excited any fluorophores present in the sample for enhancement by grating 212. In some embodiments, the beam width of excitement light source 216 provides ample coverage of grating 212. In other embodiments, mirror 218 is a scanning mirror adapted to redirect light from excitement light source 216 over a larger portion of grating 212. In still other embodiments, the angle of excitement light source 216 can be adjusted manually or directly by controller 220.

The operation of light source 216 is controlled by controller 220. Controller 220 comprises a processor such as a processor 104 and any additional circuitry necessary to provide power on demand to light source 216. In some embodiments, controller 220 further comprises a wired or wireless interface for communicating with smartphone 204. For example, controller 220 may communicate via a USB connection or a wireless protocol such as Bluetooth with smartphone 204, thereby allowing smartphone 204 to activate light source 216 only when grating 212 is aligned properly under sensor 206 and smartphone 204 is prepared to capture imagery. In some embodiments, controller 220 further communicated with temperature and humidity sensor 226 to measure the ambient conditions during the diagnostic test to ensure that they conform to the testing protocol. In other embodiments, operation of light source 216 is instead controlled by power switch 222 directly. Finally, power source 224 provides power to controller 220 and light source 216 and (where necessary) scanning mirror 218. In some embodiments, smartphone 204 acts as the power source 224 by providing power via (for example) a USB connection.

Diagnostic Process Overview

Figure 3:
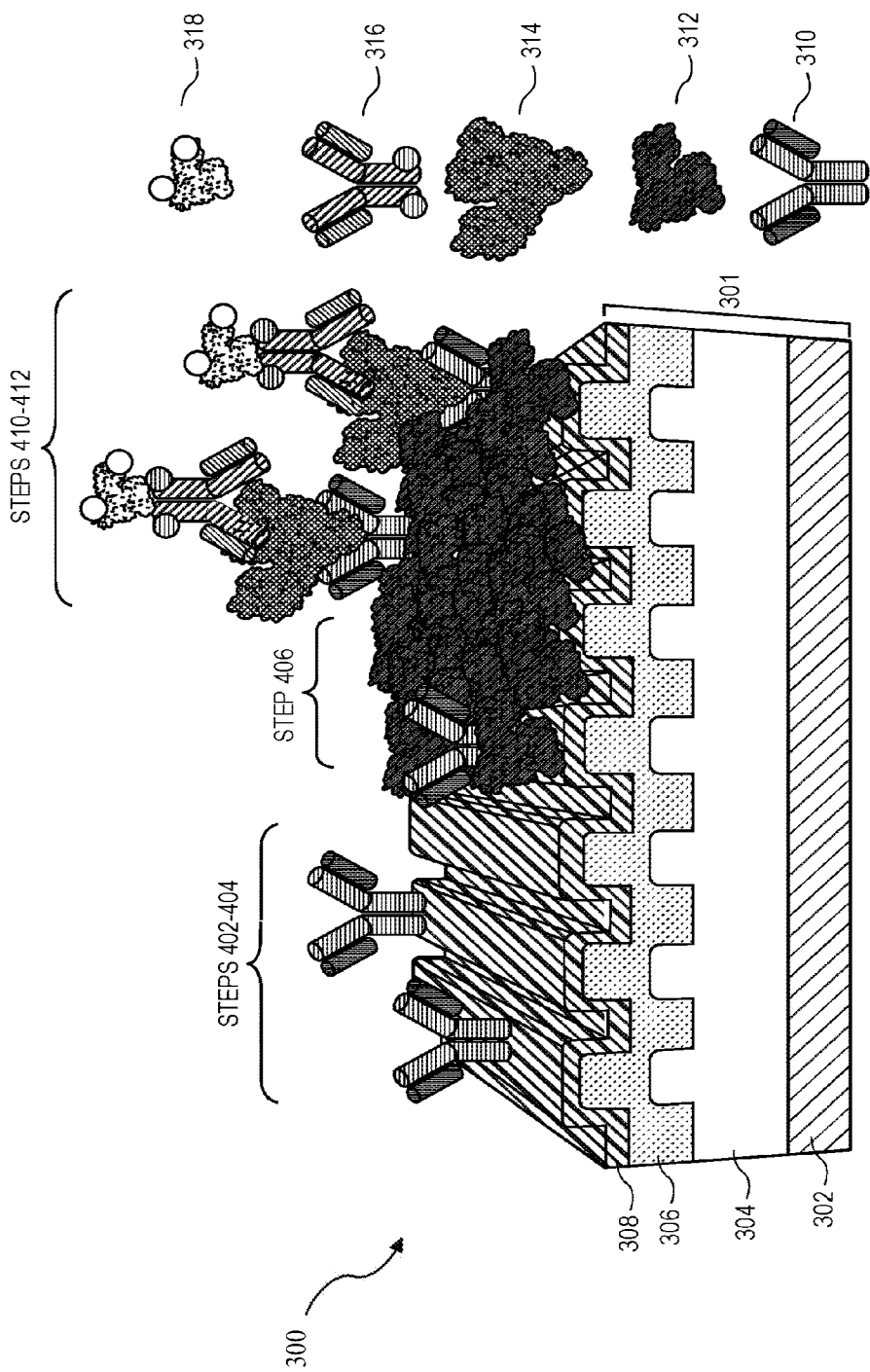
FIG. 3 depicts overview of the biomarker detection process on a sample grating.

Turning now, to FIG. 3, overview of the biomarker detection process on a sample grating is depicted and referred to generally by reference numeral 300. Note that this is a schematic diagram showing the evolution of the grating throughout the process rather than a particular time in the process. Reference numerals from flowchart 400 have been added to show how the surface changes throughout the process.

Process 300 begins with a nanoscale grating 301 comprising a number of layers. Grating 301 is discussed in greater detail elsewhere; however, a high-level summary is provided here for ease of understanding. Grating 301 is positioned on a substrate 302. In some embodiments, substrate 302 is a glass slip. In other embodiments, substrate 302 may be a wellplate, such as a 96 wellplate made of polystyrene or any other suitable material. In still other embodiments, substrate 302 may be a base of a microfluidic flow cell. Broadly speaking, and surface that provides the appropriate level of support rigidity (or flexibility) as well as adhesion to polymer layer 304 is contemplated as being within the scope of the invention.

Adhered to substrate 302 is nanoscale grating layer 304. Nanoscale grating layer 304 is discussed in greater detail in application Ser. No. 15/543,150 (incorporated by reference herein), but may be comprised of a polymer such as polymethylsilsesquioxane (PMSSQ), polyurethane, NOA 71, NOA 73 and NOA 81 or any other appropriate material. Grating layer 304 may be shaped by contact with a mold to provide the appropriate shape and structure to the grating 301 as a whole. As can be seen in FIG. 3, grating layer 304 typically comprises longitudinal peaks and valleys providing a shape conducive to fluorescence enhancement.

On top of nanoscale grating layer 304, reflective layer 306 is applied. Broadly speaking, reflective layer 306 can be any material conductive to surface plasmon resonance or any other fluorescence enhancement technique. In particular, silver, gold, platinum, aluminum or other similar metals or alloys are contemplated for use in the reflective layer 306. Alternatively, reflective layer 306 may be made of a dielectric such as titania, silica, alumina, or indium tin oxide (ITO) giving rise to the development of a photonic crystal device. In some embodiments (for example, where reflective layer 306 is susceptible to corrosion because it is made of silver), reflective layer 306 may be capped by capping later 308. Capping layer 308 may be made of any appropriately non-reactive material (such as alumina, silica, titania or, similar oxide).

Turning now to the process of biomarker detection as shown in FIG. 300 (and described in greater detail elsewhere), grating 301 is first subjected to an adhesion treatment step 402 to allow antibodies such as capture antibody 310 to adhere to the grating. Next, grating 301 is exposed to capture antibody 310, resulting in at least a fraction of the capture antibodies adhering to the surface of grating 301, as shown at the left of process 300. Next, at step 406, grating 301 is exposed to a blocking agent 312 to prevent any subsequent material (such as detection antibody 316) from adhering to the surface of grating 301 directly. Thus, only the capture antibody and the (non-reactive) blocking agent are exposed on grating 301. This is shown at the center of process 300. Grating 301 is then exposed to the sample at step 408, which may or may not contain the biomarker 314 being tested for. If the sample does contain biomarker 314, then the capture antibody will bind to and capture the biomarker 314. Next, at step 410, grating 301 is exposed to detection antibody 316, which (being another antibody for the biomarker) will bind to any biomarker molecules that have bound to the capture antibody. Finally, at step 412, the grating is exposed to the fluorophore 318, which is selected to as to bind to or react with the detection antibody 316. Thus, at the completion of this process, grating 301 will have bound to it a portion of the fluorophore 318 if the sample contained the biomarker 314. If, on the other hand the sample did not contain the biomarker, then there is nothing for detection antibody 316 (and, therefore fluorophore 318) to bind to and the sample will not fluoresce when exposed to a light source such as light source 216.

Figure 4:
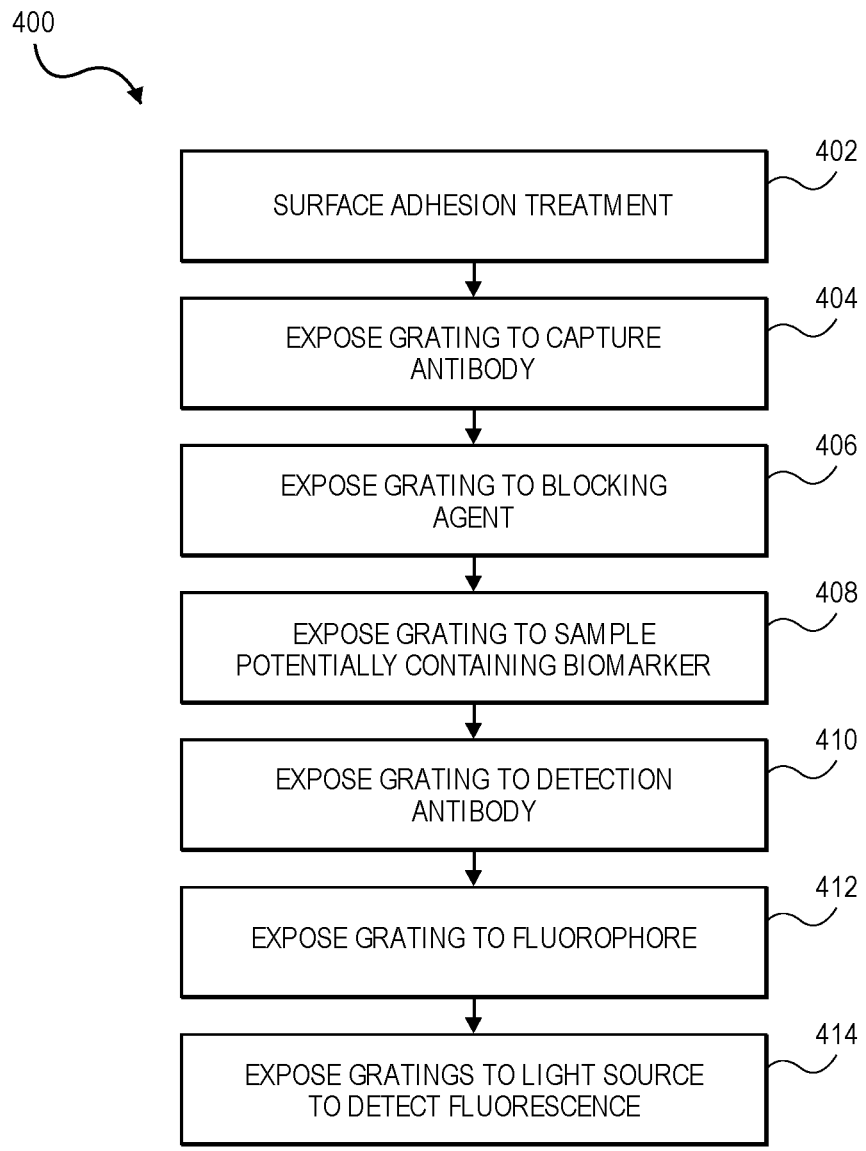
FIG. 4 depicts a flowchart depicting the process of detecting a biomarker in a sample using a fluorescence-enhancing nanoscale grating.

Turning now to FIG. 4, a flowchart depicting the process of detecting a biomarker in a sample using a fluorescence-enhancing nanoscale grating is depicted and referred to generally by reference numeral 400. The depicted embodiment begins by subjecting the grating (such as grating 301) to an adhesion treatment to increase the binding of capture antibodies to the surface of the grating. This treatment may occur as a part of the grating manufacture process or in the field in various embodiments. In some embodiments, adhesion treatment step 402 comprises treatment with poly-L-lysine. For example, the gratings may be exposed to a solution of PLL at a concentration of 100, 50, 4, 2, or 1 µg/mL overnight at a temperature of 4° C. prior to being rinsed. In some embodiments, the gratings may also be exposed to cross-linking agents such as 1-ethyl-3(3-dimethylaminopropyl)-carbodiimide (EDC), N-hydroxysuccinimide (NHS) and/or 2-(N-morpholino) ethanesulfonic acid) (MES). In some such embodiments, this treatment is followed up by treatment with sodium bicarbonate buffer (for example buffered to a pH of 9.6) and/or a commercial plate stabilizer such as AbGuard®.

In other embodiments, adhesion treatment step 402 comprises a hydrophilicity treatment such as exposure to argon, oxygen, or carbon dioxide plasma (via, for example, between a 30-second and 5-minute treatment of 7-watt plasma-enhanced chemical vapor deposition) to create hydroxyl groups. In some such embodiments, the surface is further treated with a cross-linker such as (3-Aminopropyl) triethoxysilane (APTES) to convert hydroxyl groups to amine groups.

In still other embodiments, adhesion treatment step 402 comprises coating grating 301 in a thin film (e.g., 1 nm, 2 nm, 3 nm, 5 nm, 20 nm or otherwise from 0.1-40 nm) of another polymer. For example, polymers such as such as polystyrene, polycarbonate, poly(methyl methacrylate) (PMMA) or PMSSQ can be used. In other embodiments, a small number of layers (e.g., 1, 2, 3, 4, or 5 or more) of a two-dimensional material such as functionalized graphene (e.g., carboxylated graphene oxide (GO—COOH)), molybdenum trioxide ($MoO_3$), or molybdenum disulfide ($MoS_2$) may be added. Alternatively or in addition, a nanoparticle such as 1-3 nm diameter PMSSQ based organosilicate nanoparticles (OSNP) may be applied (via, for example, spin coating). This thin film (whether it is polymer, two-dimensional material, nanoparticle, or any combination of these) may then be subjected to either plasma treatment (as discussed above) or exposed to radiation. In the latter case, exposure to 18 to 30 kiloGrays from an x-ray source (either from a gamma source or from an alpha or beta ray source) to convert a portion of the carbon atoms to oxygen, thereby converting aromatic and aliphatic groups to alcohol, ether, carbonyl and/or ester/acid groups. As described above, in some such embodiments, the surface is further treated with a cross-linker such as APTES to convert hydroxyl groups to amine groups and further increase adhesion.

The process can then proceed to step 404, where the adhesion-treated grating can be exposed to the capture antibody (such as capture antibody 310). Broadly speaking, the capture antibody must be selected to be sensitive to the biomarker which is under test. For example, Lipoarabinomannan (LAM) and Interferon gamma (IFN-g) are biomarkers for tuberculosis (TB) diagnosis. As such, anti-LAM antibodies may be used when testing for elevated LAM levels, and anti-IFN-g antibodies may be used when testing for abnormal IFN-g levels. Antibodies for various biomarkers are typically available for sale commercially. After exposure, when sufficient capture antibody has adhered to grating 301, grating 301 may be washed with a buffer such as phosphate-buffered saline (PBS) in some embodiments to remove the excess antibody. In some such embodiments, the washing solution used throughout additionally includes a surfactant such as polysorbate 20. In some embodiment, the antibodies are exposed to EDC/Sulfo-NHS to activate surface carboxyl groups for increased binding to the amine surface present on the gratings.

Next, at step 406, the grating is exposed to a stabilizer and/or blocking agent. In some embodiments, this stabilizer is a 0.1M sodium bicarbonate conjugation buffer titrated to 9.6 pH used to immobilize the antibodies. In some embodiments, the blocking agent is PBS with 3% bovine serum albumin (BSA). In other embodiments, a commercially available plate stabilizer such as AbGuard® is used instead. This blocking agent prevents the adhesion-treated grating from binding to any later additions, which could cause a false positive reading for the biomarker.

The process then continues to step 408, where the grating is exposed to the sample under test. The goal of the diagnostic method may to determine whether the sample contains the biomarker 314, what the levels of biomarker 314 in the sample are, or to determine how the levels of the biomarker 314 in the sample are changing over time. As such, the sample may be any medium extracted from a patient where the levels of the sample are of diagnostic utility. For example, the sample may be blood, saliva, urine, or any other bodily fluid. The sample may also be processed bodily tissue. For example, a biopsy may extract cells from a suspect tissue culture which are then subjected to lysis to break open the cell walls to detect a particular intra-cellular biomarker. Broadly speaking, any biomarker is contemplated as being within the scope of the invention. Because of the antibody adhered to the grating, the result of this step is that a portion of the biomarker in the sample (if any) will be adhered to the grating via the capture antibody. In some embodiments, the grating may be rinsed with PBS after this step.

Next, at step 410, the grating is exposed to the detection antibody 316. Like the capture antibody 310, detection antibody 316 is selected such that it is sensitive to biomarker 314. In some embodiments, detection antibody 316 binds to the same antigen as capture antibody 310. In other embodiments, detection antibody 316 binds to a different antigen present in biomarker 314 than that bound to by capture antibody 310. Detection antibody is also detectable in some way via visible light. For example, detection antibody 316 may be a biotinylated antibody. Such antibodies react with fluorophores (such as fluorophore 318) rendering them fluorescent under appropriate light. In other cases, the detection antibody may itself be a fluorophore. At the end of this step, grating 301 has adhered to it a portion of the detection antibody only if the sample included the biomarker. In some embodiments, the grating may be rinsed with PBS after this step to remove any unbound detection antibody 316.

The process then proceeds to step 412, where the grating is exposed to fluorophore 318. Different fluorophores may be used depending on the labeling of detection antibody 316. Where, for example, detection antibody 316 is conjugated with biotin, a fluorophore such as (Rhodamine Red™-X)-Streptavidin or Alexa Fluor® 594. Alternatively, a fluorophore such as Tetramethylrhodamine (TRITC) or Fluorescein isothiocyanate (FITC) may be used. The choice of fluorophore may depend on whether multiple biomarkers are simultaneously being tested for. At the conclusion of this step, grating 310 now has fluorophores bound to its surface if and only if the sample contained the biomarker.

Finally, at step 414, the grating can be exposed to a light source such as light source 216 to check for fluorescence (and by contrast for the presence of biomarker 314). In some embodiments, the color (i.e., the wavelength) of light source 216 is determined based on fluorophore 318, as each fluorophore will typically have its own characteristic excitation and emissions peak wavelengths. Because of the fluorescence-enhancing properties of grating 301 (which, as described above, can enhance fluorescence by a factor of 100 or more), detection of biomarkers is made significantly easier than where the fluorescent sandwich ELISA assay is carried out on a glass slide.

With regards to FIG. 4, it is to be understood that, although each of the disclosed steps is described as being carried out in sequence, it certain embodiments, they may be carried out simultaneously. For example, although the process as described exposes the grating to the detection antibody and then to the fluorophore, other embodiments may expose the grating to both of these elements simultaneously. Alternatively, in some embodiments, the detection antibody may itself be fluorescent and so no separate fluorophore is necessary. Such embodiments are contemplated as being within the scope of the invention.

Figure 5:
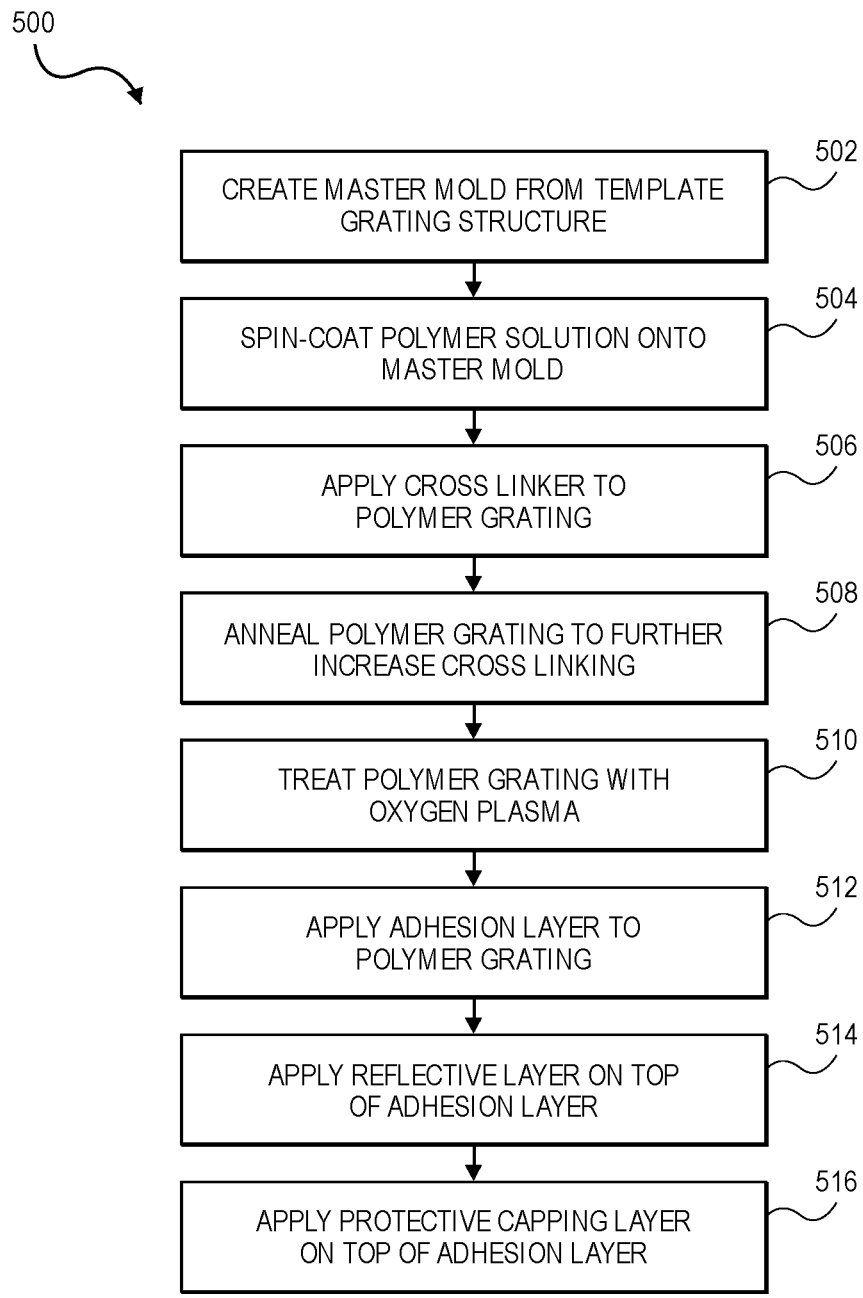
FIG. 5 depicts a flowchart depicting a method of fabricating flexible nanograting structures in accordance with embodiments of the invention.

Turning now to FIG. 5, a flowchart depicting a method of fabricating flexible nanograting structures in accordance with embodiments of the invention is depicted and referred to generally by reference numeral 500. Initially, at step 502, a master mold (also called a stamp) is created from a template grating structure by applying a plastic material to the template grating structure. The plastic material may be any flexible, somewhat resilient polymer that can adapt to the shape of a mold and retain that shape. An exemplary plastic material is polydimethylsiloxane (PDMS), although other flexible polymers can also be used. The template grating structure may be any solid object including an appropriate nanograting pattern, and may be created via patterning and etching, electron-beam lithography, reactive ion etching, machining, or other techniques. A master mold may also be re-purposed from a commercial product containing appropriate grating patterns, such as a compact disc (CD), a digital video disc (DVD), a high definition DVD (HD-DVD), a Blu-Ray™ disc, etc., which includes an internal data layer defined by a grating pattern. Techniques for creating a master mold are further discussed in the related U.S. patent application Ser. No. 14/081,353 as incorporated by reference above.

Once the plastic material has been applied to the template grating structure to create the master mold, the master mold can be cured appropriately based on the plastic material. For example, if PDMS is used for the plastic material, the master mold may be cured at room temperature under controlled humidity (for example, at 60% relative humidity) to allow appropriate hydrosilylation (also known as "crosslinking") reactions to take place to improve the mechanical properties of the PDMS. Other plastic materials may be cured differently, such as via the application of curing catalysts or curing agents, ultraviolet or other light, or simply via time. Some plastic materials may have acceptable mechanical properties immediately and may not require a curing process.

Once the master mold has been created, a polymer can be applied to the master mold to create the base layer of the grating structure at step 504. For example, poly(methylsilsesquioxane) (PMSSQ), nitrocellulose, THV (a polymer of tetrafluoroethylene, hexafluoropropylene and vinylidene fluoride), polytetrafluoroethylene (PTFE or Teflon), Polyvinyl Alcohol (PVA), or similar polymer can be used as the polymer. If PMSSQ is used, it can be dissolved in an appropriate solvent (such as ethanol, propylene glycol monomethyl ether acetate (PGMEA) or other appropriate solvent) and spin coated onto the master mold. The polymer can be applied either immediately or after the solvent has evaporated and the plastic has reached an appropriate degree of crosslinking on the master mold to an appropriate substrate (such as a glass slide or a silicon wafer) and removed from the master mold. Techniques for transferring the polymer grating from the master mold to the substrate are also discussed in greater detail in the related U.S. patent application Ser. No. 14/081,353 as incorporated by reference above. Regardless of the techniques used, at the end of step 504, a polymer grating on a substrate has been obtained. This polymer grating has a highly accurate replication of the desired nanograting structure, but poor mechanical properties due to a lack of crosslinking in the polymer.

To improve the mechanical properties of the polymer grating and prevent mechanical damage or reflow of the polymer from changing the nanograting structure, the crosslinking of the polymer grating can be improved. At step 506, a chemical crosslinker (such as 3-aminopropyltriethoxysilane (APTES) for PMSSQ, trimethylchlorosilane (TMCS), or another crosslinker appropriate to the polymer used) is applied to the polymer grating. In some embodiments, the crosslinker is applied in vapor form. In such embodiments, the polymer gratings can be placed in a vacuum chamber with an open container of the crosslinker. A vacuum can then be applied to encourage evaporation of the crosslinker, and then the vacuum can be turned off to allow for vapor movement. In one such embodiment, the vacuum is applied for ten minutes and removed for ten minutes, and this process is repeated for one hour. In another embodiment, vacuum is applied for 10 minutes (until a pressure of approximately −81 kilopascals is reached), and maintained for one hour. In some embodiments, the vapor pressure of the crosslinker can further be increased by mixing it with a solvent (such as ethanol) with high vapor pressure.

Next, at step 508, crosslinking can be further increased internally in the polymer gratings via the process of thermally annealing them. In some embodiments, the process of annealing the polymer gratings begins with a relatively low-temperature, high-duration annealing step. For example, the gratings may be heated to 60 degrees Celsius for three hours. This allows for the evaporation of any remaining solvent from the spin-coating process and initiates crosslinking in the gratings without subjecting them to heat levels that would cause reflow of the polymer. In some embodiments, the grating can then be subjected to a second annealing step at a higher temperature for a shorter time. For example, the gratings may be gradually heated (e.g., at a rate of 1 degree Celsius per minute) to a temperature of 400 degrees Celsius and kept there for one hour. In other embodiments, the second annealing step can take place at 200 degree Celsius, at 550 degrees Celsius, at 600 degrees Celsius, or at any other temperature to achieve the desired crosslinking without breaking down the polymer. The crosslinking process of steps 506 and 508 improve the mechanical properties of the polymer gratings without appreciably changing the nanograting structures, resulting in stable polymer gratings that can be used in high-temperature processes such as atomic layer deposition (ALD), electron-beam deposition, thermal and sputtering deposition of metals and dielectric materials, including but not limited to gold, silver, platinum, silica, alumina, titania, indium tin oxide (ITO), and diamond like carbon (DLC).

When used in optical applications, a reflective layer is typically applied to the polymer gratings to couple better with photons and enhance fluorescence. However, adhesion between typical metallic reflective layer materials and untreated polymer gratings is typically poor due to the hydrophobic surface layer of the polymer. For example, when PMSSQ is used, the non-polar surface methyl groups render the polymer grating hydrophobic. To improve adhesion, these surface methyl groups can be rendered polar (and the surface thereby rendered hydrophilic) via oxidation. In some embodiments, step 510 treats the polymer grating with a hydrophilicity agent, such as plasma (such as oxygen or carbon dioxide plasma) or ozone to convert surface methyl groups to hydroxyl groups and carboxyl groups. For example, the polymer gratings can be treated by oxygen plasma for 30 seconds at a power of seven watts.

Once the surface has been rendered hydrophilic, an adhesion layer may, in some embodiments, be applied to the plasma-treated polymer grating at step 512. The adhesion layer allows for better overall adhesion than if the reflective layer were applied directly to the (potentially plasma-treated) polymer grating. In grating 301 as depicted in FIG. 3, no adhesion layer is depicted; however, gratings with such adhesion layers are contemplated. In some embodiments, chromium is used for the adhesion layer. In other embodiments, other materials such as chromium (III) oxide (also called chromia), germanium, titanium, or titanium (IV) oxide (also called titania) can be used. In some embodiments, the adhesion layer is approximately five nanometers thick. In other embodiments, it is approximately ten nanometers thick to approximately fifteen nanometers thick. Any of a variety of known techniques can be used for the application of the adhesion layer. For example, thermal evaporation can be used to deposit the adhesion layer on the plasma-treated polymer grating. When using such a process, the adhesion layer may be deposited at a rate of approximately 0.005 nanometers per second.

Once the adhesion layer has been applied, the reflective layer can be applied on top of the adhesion layer at step 514. In some embodiments, the reflective layer can be made of silver. In other embodiments, the reflective layer can be made of gold or platinum, or from a mixture of these and other materials, as discussed above. In some embodiments, the reflective layer is approximately 100 nanometers thick. In other embodiments, the reflective layer is 10 nanometers thick to 300 nanometers thick. Other thicknesses may also be used depending on the application and the materials used. In some embodiments, the adhesion layer and the reflective layer can be applied sequentially for better bonding. For example, in the example above, the thermal deposition of chromium at a rate of 0.005 nanometers per second can immediately proceed to a deposition of a silver reflective layer at 0.005-0.01 nanometers per second until five nanometers of the silver reflective layer have been deposited, and then the rate of deposition increased to 0.05 nanometers per second until the desired thickness of the reflective layer has been reached.

The nanograting structure thus produced has good structural and reflective properties, but is subject to degradation over time, due to oxidation and cluster formation. To preserve the grating, a protective capping layer is applied at step 516. In some embodiments, this capping layer can be made of aluminum (III) oxide (also called alumina). In other embodiments, the capping layer can be made of silicon (IV) oxide (also called silica), titanium (IV) oxide (also called titania) or other appropriate metallic or non-metallic materials. In some embodiments, the protective capping layer is approximately ten nanometers thick. In other embodiments, the capping layer is five nanometers or twenty nanometers thick. In some embodiments, the capping layer is deposited using one of the deposition techniques described above. In other embodiments, the capping layer can be deposited using other techniques, such as atomic layer deposition. When using atomic layer deposition, the reflective layer of the nanograting structure may be further annealed to promote grain growth in the reflective layer. For example, the gratings may be placed under vacuum or non-reactive atmosphere as the temperature is ramped to a desired annealing temperature (e.g., from 60 to 300 degrees Celsius) for a desired time (e.g., 2 hours).

After annealing, a first precursor can be pulsed over the surface to add functional groups and improve the surface conditions for subsequent reactions with additional precursors to form the capping layer. For example, water can be pulsed over the surface for 20 milliseconds with a wait of 8 seconds between pulses for 50 cycles to form surface hydroxyl groups. Once the surface is prepared, additional precursors can be pulsed over the surface to react with the previously created functional groups. For example, when an alumina capping layer is desired, trimethylaluminum (TMA) can be used together with water to form the capping layer. In such a case, the TMA and water can be alternately pulsed (for example, pulsing TMA for 0.0125 seconds, pulsing water for 0.02 seconds, and delaying 20 seconds between pulses). Each pulsing cycle adds a particular thickness of alumina, so the desired thickness can be controlled by altering the number of pulsing cycles. For example, if a 10 nanometer alumina layer is desired, 100 pulsing cycles may be required. When the desired thickness has been reached, a final water pulse can be used to ensure that the surface of the capping layer has hydroxyl groups rather than methyl groups. Once the capping layer has been formed, the finalized grating can be cooled.

The resulting grating may then be applied to a substrate for additional mechanical stability. In some embodiments, this application is done by adhering the grating to the substrate using an appropriate spray adhesive. As described above with respect to substrate 302, this substrate may be a glass slip, a wellplate, a flow cell, or any other appropriate substrate for mechanically supporting the grating in its ultimate applications.

As described above with respect to step 402 of process 400, the resulting grating may subsequently be treated by an additional adhesion treatment to promote adhesion of the capture antibodies. Such an adhesion treatment can be performed as part of the grating manufacture process 500 or as part of the biomarker detection process 400, depending on the precise nature of the adhesion treatment employed.

Many different arrangements of the various components depicted, as well as components not shown, are possible without departing from the scope of the claims below. Embodiments of the invention have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims. Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A method of fabricating a fluorescence-enhancing, flexible, nanoscale plasmonic grating, comprising:
    exposing a master mold to a hydrophilicity agent such that surface methyl groups of the master mold are converted to hydroxyl groups and carboxyl groups, wherein the master mold is hydrophobic prior to exposure to the hydrophilicity agent;
    spin coating the master mold with a grating material;
    curing the grating material to produce a flexible nanoscale polymer grating in the master mold;
    removing the flexible nanoscale polymer grating from the master mold;
    coating the flexible nanoscale polymer grating in a fluorescence-enhancing reflective layer;
    coating the fluorescence-enhancing reflective layer with a protective capping layer, the protective capping layer comprising a corrosion resistant material; and
    applying an adhesion layer to the protective capping layer.

2. The method of claim 1, wherein the hydrophilicity agent is oxygen plasma, and wherein the master mold is exposed to the oxygen plasma for approximately 30 seconds at a power of approximately 7 watts.

3. The method of claim 1, wherein the grating material is selected from a set consisting of Norland Optical adhesive (NOA) 71, NOA 73 and NOA 81.

4. The method of claim 1, wherein the flexible nanoscale polymer grating is between approximately 40 micrometers and approximately 110 micrometers thick.

5. The method of claim 1, wherein the method further comprises:
    positioning a plastic substrate over the grating material; and
    exposing the master mold, the grating material, and the plastic substrate to vacuum for at least ten minutes prior to curing the grating material.

6. The method of claim 1, wherein curing the grating material comprises exposing the grating material to a 6-Watt UV light source for at least 40 minutes.

7. The method of claim 1, wherein the flexible nanoscale polymer grating is between approximately 500 micrometers and 2 millimeters thick.

8. The method of claim 1, wherein the fluorescence-enhancing reflective layer is a silver layer and is approximately 100 nanometers thick.

9. The method of claim 1, comprising:
    applying the flexible nanoscale polymer grating to a flexible media.

10. The method of claim 9, wherein the flexible media comprises one of: a fiber optic cable, a polymer film, or a tape.

11. The method of claim 1, comprising:
    applying an additional adhesion layer to the flexible nanoscale polymer grating prior to coating the flexible nanoscale polymer grating in the fluorescence-enhancing reflective layer.

12. The method of claim 11, wherein the additional adhesion layer comprises at least one of: chromium, chromia, germanium, titanium, or titania.

13. The method of claim 1, wherein the protective capping layer comprises a non-reactive material that comprises at least one of: alumina, silica, or titania.

14. The method of claim 1, wherein coating the fluorescence-enhancing reflective layer with the protective capping layer comprises:
    pulsing water and trimethylaluminum over the fluorescence-enhancing reflective layer, the water and the trimethylaluminum forming an alumina capping layer, the alumina capping layer defining at least a portion of the protective capping layer comprising a non-reactive material.

15. The method of claim 1, wherein the adhesion layer is between 0.1 and 20 nanometers thick, and wherein the adhesion layer comprises at least one of: a polymer, a two-dimensional material, or a nanoparticle material.

16. The method of claim 15, wherein the adhesion layer comprises the polymer and wherein the polymer comprises polystyrene, and wherein the polymer comprises a thin film of from 1 to 5 nanometers thick.

17. The method of claim 15, wherein the adhesion layer comprises the two-dimensional material and wherein the two-dimensional material comprises carboxylated graphene oxide.

18. The method of claim 15, comprising:
   subjecting the adhesion layer to a plasma treatment or an x-ray treatment.

19. The method of claim 15, comprising:
   applying a cross-linker to the adhesion layer.

20. The method of claim 1, wherein the fluorescence-enhancing, flexible, nanoscale plasmonic grating enhances fluorescence by a factor of at least 100 as compared to a glass substrate.

* * * * *